US012779191B2

(12) United States Patent
Chan et al.

(10) Patent No.: US 12,779,191 B2
(45) Date of Patent: Nov. 3, 2026

(54) UPPER ARM PORT

(71) Applicant: Becton, Dickinson and Company, Franklin Lakes, NJ (US)

(72) Inventors: Weng Khuen Adrian Chan, Shanghai (CN); Jianjiang Chen, Shanghai (CN)

(73) Assignee: Becton, Dickinson and Company, Franklin Lakes, NJ (US)

( * ) Notice: Subject to any disclaimer, the term of this patent is extended or adjusted under 35 U.S.C. 154(b) by 131 days.

(21) Appl. No.: 18/706,739

(22) PCT Filed: Nov. 2, 2021

(86) PCT No.: PCT/CN2021/128248
§ 371 (c)(1),
(2) Date: May 1, 2024

(87) PCT Pub. No.: WO2023/077276
PCT Pub. Date: May 11, 2023

(65) Prior Publication Data

US 2026/0158257 A1 Jun. 11, 2026

(51) Int. Cl.
*A61M 39/06* (2006.01)

(52) U.S. Cl.
CPC ....... *A61M 39/06* (2013.01); *A61M 2039/066* (2013.01)

(58) Field of Classification Search
CPC ........................ A61M 39/06; A61M 2039/066
See application file for complete search history.

(56) References Cited

U.S. PATENT DOCUMENTS 3,951,147 A 4/1976 Tucker et al.
4,184,489 A 1/1980 Burd
4,222,374 A 9/1980 Sampson et al.
4,400,169 A 8/1983 Stephen
(Continued)

FOREIGN PATENT DOCUMENTS

CA 1261698 A 9/1989
CA 2318089 A1 7/1999
(Continued)

OTHER PUBLICATIONS

U.S. Appl. No. 17/763,154, filed Mar. 23, 2022 Advisory Action dated Oct. 20, 2025.

(Continued)

*Primary Examiner* — Dung T Ulsh
(74) *Attorney, Agent, or Firm* — Rutan & Tucker LLP

(57) ABSTRACT

Embodiments disclosed herein are directed to a vascular access system including a port assembly and an expansion kit. The port assembly includes a port coupled to a catheter. The port can include a septum aligned with the catheter lumen configured to receive a guidewire therethrough. The expansion kit can include a dilator disposed within a sheath. Advancing the expansion kit subcutaneously can separate the tissues and for a tissue pocket sized to receive the port assembly therein. The dilator can be removed and the port assembly can be placed within the sheath. The port can include a splitter device configured to engage an aperture disposed in the sheath. Urging the sheath proximally, the splitter can direct the sheath onto a blade facilitating separation of the sheath along a longitudinal axis.

19 Claims, 10 Drawing Sheets

(56) References Cited

U.S. PATENT DOCUMENTS

| | | | | |
|---|---|---|---|---|
| 4,447,237 | A | | 5/1984 | Frisch et al. |
| 4,496,349 | A | | 1/1985 | Cosentino |
| 4,543,088 | A | | 9/1985 | Bootman et al. |
| 4,559,039 | A | | 12/1985 | Ash et al. |
| 4,569,675 | A | | 2/1986 | Prosl et al. |
| 4,673,394 | A | | 6/1987 | Fenton, Jr. et al. |
| 4,675,004 | A | | 6/1987 | Hadford et al. |
| 4,692,146 | A | | 9/1987 | Hilger |
| 4,695,273 | A | | 9/1987 | Brown |
| 4,704,103 | A | | 11/1987 | Stober et al. |
| 4,710,174 | A | | 12/1987 | Moden et al. |
| 4,751,926 | A | | 6/1988 | Sasaki |
| 4,762,517 | A | | 8/1988 | McIntyre et al. |
| 4,767,410 | A | | 8/1988 | Moden et al. |
| 4,772,270 | A | | 9/1988 | Wiita et al. |
| 4,772,276 | A | | 9/1988 | Wiita et al. |
| 4,778,452 | A | | 10/1988 | Moden et al. |
| 4,790,826 | A | | 12/1988 | Elftman |
| 4,802,885 | A | | 2/1989 | Weeks et al. |
| 4,804,054 | A | | 2/1989 | Howson et al. |
| 4,820,273 | A | | 4/1989 | Reinicke |
| 4,861,341 | A | | 8/1989 | Woodburn |
| 4,886,501 | A | | 12/1989 | Johnston et al. |
| 4,892,518 | A | | 1/1990 | Cupp et al. |
| 4,897,081 | A | | 1/1990 | Poirier et al. |
| 4,904,241 | A | | 2/1990 | Bark |
| 4,915,690 | A | | 4/1990 | Cone et al. |
| 4,929,236 | A | | 5/1990 | Sampson |
| 4,963,133 | A | | 10/1990 | Whipple |
| 4,978,338 | A | | 12/1990 | Melsky et al. |
| 4,997,424 | A | | 3/1991 | Little |
| 5,013,298 | A | | 5/1991 | Moden et al. |
| 5,041,098 | A | | 8/1991 | Loiterman et al. |
| 5,045,060 | A | | 9/1991 | Melsky et al. |
| 5,045,064 | A | | 9/1991 | Idriss |
| 5,053,013 | A | | 10/1991 | Ensminger et al. |
| 5,057,084 | A | | 10/1991 | Ensminger et al. |
| 5,084,015 | A | | 1/1992 | Moriuchi |
| 5,090,954 | A | | 2/1992 | Geary |
| 5,108,377 | A | | 4/1992 | Cone et al. |
| 5,137,529 | A | | 8/1992 | Watson et al. |
| 5,147,321 | A | | 9/1992 | Slonina et al. |
| 5,147,483 | A | | 9/1992 | Melsky et al. |
| 5,158,547 | A | | 10/1992 | Doan et al. |
| 5,167,633 | A | | 12/1992 | Mann et al. |
| 5,167,638 | A | | 12/1992 | Felix et al. |
| 5,171,228 | A | | 12/1992 | McDonald |
| 5,178,612 | A | | 1/1993 | Fenton, Jr. |
| 5,180,365 | A | | 1/1993 | Ensminger et al. |
| 5,185,003 | A | | 2/1993 | Brethauer |
| 5,201,715 | A | | 4/1993 | Masters |
| 5,203,771 | A | | 4/1993 | Melker et al. |
| 5,213,574 | A | | 5/1993 | Tucker |
| D337,637 | S | | 7/1993 | Tucker |
| 5,226,879 | A | | 7/1993 | Ensminger et al. |
| 5,263,930 | A | | 11/1993 | Ensminger |
| 5,266,071 | A | | 11/1993 | Elftman |
| 5,281,199 | A | | 1/1994 | Ensminger et al. |
| 5,281,205 | A | | 1/1994 | McPherson |
| 5,312,355 | A | | 5/1994 | Lee |
| 5,318,545 | A | | 6/1994 | Tucker |
| 5,336,194 | A | | 8/1994 | Polaschegg et al. |
| 5,350,360 | A | | 9/1994 | Ensminger et al. |
| 5,360,407 | A | | 11/1994 | Leonard et al. |
| 5,387,192 | A | | 2/1995 | Glantz et al. |
| 5,395,324 | A | | 3/1995 | Hinrichs et al. |
| 5,399,168 | A | | 3/1995 | Wadsworth, Jr. et al. |
| 5,405,325 | A | | 4/1995 | Labs |
| 5,409,463 | A | | 4/1995 | Thomas et al. |
| 5,417,656 | A | | 5/1995 | Ensminger et al. |
| 5,421,814 | A | | 6/1995 | Geary |
| 5,423,334 | A | | 6/1995 | Jordan |
| 5,441,504 | A | * | 8/1995 | Pohndorf .......... A61M 25/0668 604/167.03 |
| 5,476,451 | A | | 12/1995 | Ensminger et al. |
| 5,503,630 | A | | 4/1996 | Ensminger et al. |
| 5,514,103 | A | | 5/1996 | Srisathapat et al. |
| 5,520,643 | A | | 5/1996 | Ensminger et al. |
| 5,527,277 | A | | 6/1996 | Ensminger et al. |
| 5,527,278 | A | | 6/1996 | Ensminger et al. |
| 5,531,684 | A | | 7/1996 | Ensminger et al. |
| 5,542,923 | A | | 8/1996 | Ensminger et al. |
| 5,554,117 | A | | 9/1996 | Ensminger et al. |
| 5,556,381 | A | | 9/1996 | Ensminger et al. |
| 5,558,641 | A | | 9/1996 | Glantz et al. |
| 5,562,617 | A | | 10/1996 | Finch, Jr. et al. |
| 5,562,618 | A | | 10/1996 | Cai et al. |
| 5,575,770 | A | | 11/1996 | Melsky et al. |
| 5,578,070 | A | | 11/1996 | Utterberg |
| 5,607,393 | A | | 3/1997 | Ensminger et al. |
| 5,613,945 | A | | 3/1997 | Cai et al. |
| 5,620,419 | A | | 4/1997 | Lui et al. |
| 5,632,729 | A | | 5/1997 | Cai et al. |
| 5,647,855 | A | | 7/1997 | Trooskin |
| 5,695,490 | A | | 12/1997 | Flaherty et al. |
| 5,702,363 | A | | 12/1997 | Flaherty |
| 5,704,915 | A | | 1/1998 | Melsky et al. |
| 5,713,858 | A | | 2/1998 | Heruth et al. |
| 5,718,682 | A | | 2/1998 | Tucker |
| 5,725,507 | A | | 3/1998 | Petrick |
| 5,741,228 | A | | 4/1998 | Lambrecht et al. |
| 5,743,873 | A | | 4/1998 | Cai et al. |
| 5,758,667 | A | | 6/1998 | Slettenmark |
| 5,769,823 | A | | 6/1998 | Otto |
| 5,792,104 | A | | 8/1998 | Speckman et al. |
| 5,810,789 | A | | 9/1998 | Powers et al. |
| 5,833,654 | A | | 11/1998 | Powers et al. |
| 5,848,989 | A | | 12/1998 | Villani |
| 5,906,596 | A | | 5/1999 | Tallarida |
| 5,908,414 | A | | 6/1999 | Otto et al. |
| 5,913,998 | A | | 6/1999 | Butler et al. |
| 5,925,017 | A | | 7/1999 | Kriesel et al. |
| 5,931,829 | A | | 8/1999 | Burbank et al. |
| 5,944,688 | A | | 8/1999 | Lois |
| 5,947,953 | A | | 9/1999 | Ash et al. |
| 5,951,512 | A | | 9/1999 | Dalton |
| 5,954,687 | A | | 9/1999 | Baudino |
| 5,954,691 | A | | 9/1999 | Prosl |
| 5,968,011 | A | | 10/1999 | Larsen et al. |
| 5,989,206 | A | | 11/1999 | Prosl et al. |
| 5,989,216 | A | | 11/1999 | Johnson et al. |
| 5,989,239 | A | | 11/1999 | Finch et al. |
| 6,007,516 | A | | 12/1999 | Burbank et al. |
| 6,013,051 | A | | 1/2000 | Nelson |
| 6,013,058 | A | | 1/2000 | Prosl et al. |
| 6,022,335 | A | | 2/2000 | Ramadan |
| 6,039,712 | A | | 3/2000 | Fogarty et al. |
| 6,042,569 | A | | 3/2000 | Finch, Jr. et al. |
| 6,053,901 | A | | 4/2000 | Finch, Jr. et al. |
| 6,056,717 | A | | 5/2000 | Finch et al. |
| 6,086,555 | A | | 7/2000 | Eliasen et al. |
| 6,090,067 | A | | 7/2000 | Carter |
| 6,090,068 | A | | 7/2000 | Chanut |
| 6,102,884 | A | | 8/2000 | Squitieri |
| 6,120,492 | A | | 9/2000 | Finch et al. |
| 6,190,349 | B1 | | 2/2001 | Ash et al. |
| 6,190,352 | B1 | | 2/2001 | Haarala et al. |
| 6,206,851 | B1 | | 3/2001 | Prosl |
| 6,213,973 | B1 | | 4/2001 | Eliasen et al. |
| D445,175 | S | | 7/2001 | Bertheas |
| 6,287,293 | B1 | | 9/2001 | Jones et al. |
| 6,332,874 | B1 | | 12/2001 | Eliasen et al. |
| 6,350,251 | B1 | | 2/2002 | Prosl et al. |
| 6,352,521 | B1 | | 3/2002 | Prosl |
| 6,398,764 | B1 | | 6/2002 | Finch, Jr. et al. |
| 6,436,084 | B1 | | 8/2002 | Finch et al. |
| 6,438,397 | B1 | | 8/2002 | Bosquet et al. |
| 6,459,917 | B1 | | 10/2002 | Gowda et al. |
| 6,478,783 | B1 | | 11/2002 | Moorehead |
| 6,482,197 | B2 | | 11/2002 | Finch et al. |
| 6,494,867 | B1 | | 12/2002 | Elver et al. |
| 6,506,182 | B2 | | 1/2003 | Estabrook et al. |
| 6,527,754 | B1 | | 3/2003 | Tallarida et al. |
| 6,540,717 | B2 | | 4/2003 | Sherry |

(56) References Cited

U.S. PATENT DOCUMENTS

| | | | |
|---|---|---|---|
| 6,562,023 | B1 | 5/2003 | Marrs et al. |
| 6,565,525 | B1 | 5/2003 | Burbank et al. |
| 6,582,409 | B1 | 6/2003 | Squitieri |
| 6,607,504 | B2 | 8/2003 | Haarala et al. |
| 6,620,118 | B1 | 9/2003 | Prosl et al. |
| 6,695,832 | B2 | 2/2004 | Schon et al. |
| 6,699,218 | B2 | 3/2004 | Flaherty et al. |
| 6,719,749 | B1 | 4/2004 | Schweikert et al. |
| 6,726,711 | B1 | 4/2004 | Langenbach et al. |
| 6,758,841 | B2 | 7/2004 | Haarala et al. |
| 6,783,522 | B2 | 8/2004 | Fischell |
| 6,852,106 | B2 | 2/2005 | Watson et al. |
| 6,881,211 | B2 | 4/2005 | Schweikert et al. |
| 6,929,631 | B1 | 8/2005 | Brugger et al. |
| 6,960,185 | B2 | 11/2005 | Adaniya et al. |
| 6,962,580 | B2 | 11/2005 | Adams et al. |
| 6,997,914 | B2 | 2/2006 | Smith et al. |
| 7,018,374 | B2 | 3/2006 | Schon et al. |
| 7,056,316 | B1 | 6/2006 | Burbank et al. |
| 7,070,591 | B2 | 7/2006 | Adams et al. |
| 7,083,648 | B2 | 8/2006 | Yu et al. |
| 7,108,686 | B2 | 9/2006 | Burke et al. |
| 7,131,962 | B1 | 11/2006 | Estabrook et al. |
| 7,223,257 | B2 | 5/2007 | Shubayev et al. |
| 7,261,705 | B2 | 8/2007 | Edoga et al. |
| 7,311,702 | B2 | 12/2007 | Tallarida et al. |
| 7,322,953 | B2 | 1/2008 | Redinger |
| D562,443 | S | 2/2008 | Zinn et al. |
| 7,347,843 | B2 | 3/2008 | Adams et al. |
| 7,351,233 | B2 | 4/2008 | Parks |
| 7,396,359 | B1 | 7/2008 | Derowe et al. |
| D574,950 | S | 8/2008 | Zawacki et al. |
| D578,203 | S | 10/2008 | Bizup |
| 7,445,614 | B2 | 11/2008 | Bunodiere et al. |
| D582,032 | S | 12/2008 | Bizup et al. |
| 7,497,850 | B2 | 3/2009 | Halili |
| D612,479 | S | 3/2010 | Zawacki et al. |
| 7,699,821 | B2 | 4/2010 | Nowak |
| 7,704,225 | B2 | 4/2010 | Kantrowitz |
| 7,708,722 | B2 | 5/2010 | Glenn |
| 7,713,251 | B2 | 5/2010 | Tallarida et al. |
| 7,731,680 | B2 | 6/2010 | Patton |
| 7,762,999 | B2 | 7/2010 | Byrum |
| 7,824,365 | B2 | 11/2010 | Haarala et al. |
| 7,846,139 | B2 | 12/2010 | Zinn et al. |
| 7,850,666 | B2 | 12/2010 | Schon et al. |
| 7,909,804 | B2 | 3/2011 | Stats |
| 7,959,615 | B2 | 6/2011 | Stats et al. |
| 7,972,315 | B2 | 7/2011 | Birk et al. |
| 7,981,094 | B2 | 7/2011 | Chelak |
| D650,475 | S | 12/2011 | Smith et al. |
| 8,075,536 | B2 | 12/2011 | Gray et al. |
| 8,079,990 | B2 | 12/2011 | Powley et al. |
| 8,147,455 | B2 | 4/2012 | Butts et al. |
| 8,152,792 | B1 | 4/2012 | Kornel |
| 8,257,325 | B2 | 9/2012 | Schweikert et al. |
| 8,277,425 | B2 | 10/2012 | Girard et al. |
| 8,328,768 | B2 | 12/2012 | Quigley et al. |
| 8,337,464 | B2 | 12/2012 | Young et al. |
| 8,337,465 | B2 | 12/2012 | Young et al. |
| 8,337,470 | B2 | 12/2012 | Prasad et al. |
| 8,343,108 | B2 | 1/2013 | Rosenberg et al. |
| 8,364,230 | B2 | 1/2013 | Simpson et al. |
| 8,377,034 | B2 | 2/2013 | Tallarida et al. |
| 8,425,416 | B2 | 4/2013 | Brister et al. |
| 8,425,476 | B2 | 4/2013 | Glenn |
| 8,480,560 | B2 | 7/2013 | Vendely |
| 8,550,981 | B2 | 10/2013 | Woodruff et al. |
| 8,574,204 | B2 | 11/2013 | Bourne et al. |
| RE44,639 | E | 12/2013 | Squitieri |
| 8,622,980 | B2 | 1/2014 | Zinn |
| 8,690,815 | B2 | 4/2014 | Porter et al. |
| 8,690,816 | B2 | 4/2014 | Dakin et al. |
| 8,738,151 | B2 | 5/2014 | Nelson |
| 8,979,806 | B2 | 3/2015 | Saab |
| 9,033,931 | B2 | 5/2015 | Young et al. |
| 9,061,129 | B2 | 6/2015 | Lauer |
| 9,072,880 | B2 | 7/2015 | Phillips et al. |
| 9,072,881 | B2 | 7/2015 | Dalton et al. |
| 9,078,982 | B2 | 7/2015 | Lane et al. |
| 9,089,395 | B2 | 7/2015 | Honaryar |
| 9,095,665 | B2 | 8/2015 | Pages et al. |
| 9,138,563 | B2 | 9/2015 | Glenn |
| 9,168,365 | B2 | 10/2015 | Bourne et al. |
| 9,174,037 | B2 | 11/2015 | Schutz et al. |
| 9,179,901 | B2 | 11/2015 | Young et al. |
| 9,180,248 | B2 | 11/2015 | Moberg et al. |
| 9,474,888 | B2 | 10/2016 | Wiley et al. |
| 9,579,496 | B2 | 2/2017 | Evans et al. |
| 9,707,339 | B2 | 7/2017 | Chartrand et al. |
| 9,987,467 | B2 | 6/2018 | Jochum |
| 10,207,095 | B2 | 2/2019 | Barron et al. |
| 10,272,236 | B2 | 4/2019 | Davey |
| 10,463,845 | B2 | 11/2019 | Stats et al. |
| D870,264 | S | 12/2019 | Fedor et al. |
| D885,557 | S | 5/2020 | Fedor et al. |
| 10,967,152 | B2 | 4/2021 | Korkuch |
| 11,090,466 | B1 | 8/2021 | Nicholson |
| 11,420,033 | B2 | 8/2022 | Fedor et al. |
| 11,464,960 | B2 | 10/2022 | Fedor et al. |
| 2001/0041870 | A1 | 11/2001 | Gillis et al. |
| 2001/0056266 | A1 | 12/2001 | Tallarida et al. |
| 2002/0099326 | A1 | 7/2002 | Wilson et al. |
| 2003/0023208 | A1 | 1/2003 | Osypka et al. |
| 2003/0181878 | A1 | 9/2003 | Tallarida et al. |
| 2004/0054352 | A1 | 3/2004 | Adams et al. |
| 2004/0073196 | A1 | 4/2004 | Adams et al. |
| 2004/0199129 | A1 | 10/2004 | DiMatteo |
| 2004/0204692 | A1 | 10/2004 | Eliasen |
| 2004/0254536 | A1 | 12/2004 | Conlon et al. |
| 2004/0254537 | A1 | 12/2004 | Conlon et al. |
| 2005/0075614 | A1 | 4/2005 | Bunodiere et al. |
| 2005/0113806 | A1 | 5/2005 | De Carvalho et al. |
| 2005/0131352 | A1 | 6/2005 | Conlon et al. |
| 2005/0148956 | A1 | 7/2005 | Conlon et al. |
| 2005/0148957 | A1 | 7/2005 | Girard et al. |
| 2005/0171502 | A1 | 8/2005 | Daly et al. |
| 2005/0203484 | A1 | 9/2005 | Nowak |
| 2005/0209573 | A1 | 9/2005 | Brugger et al. |
| 2005/0256451 | A1 | 11/2005 | Adams et al. |
| 2005/0277899 | A1 | 12/2005 | Conlon et al. |
| 2006/0084929 | A1 | 4/2006 | Eliasen |
| 2006/0089619 | A1 | 4/2006 | Ginggen |
| 2006/0100592 | A1 | 5/2006 | Eliasen |
| 2006/0173424 | A1 | 8/2006 | Conlon |
| 2006/0178617 | A1 | 8/2006 | Adams et al. |
| 2006/0178647 | A1 | 8/2006 | Stats |
| 2006/0184142 | A1 | 8/2006 | Schon et al. |
| 2006/0217659 | A1 | 9/2006 | Patton |
| 2006/0217673 | A1 | 9/2006 | Schulze et al. |
| 2006/0224129 | A1 | 10/2006 | Beasley et al. |
| 2006/0247584 | A1 | 11/2006 | Sheetz et al. |
| 2006/0264898 | A1 | 11/2006 | Beasley et al. |
| 2006/0271012 | A1 | 11/2006 | Canaud et al. |
| 2006/0293626 | A1 | 12/2006 | Byrum et al. |
| 2007/0049806 | A1 | 3/2007 | Adams et al. |
| 2007/0073250 | A1 | 3/2007 | Schneiter |
| 2007/0078391 | A1 | 4/2007 | Wortley et al. |
| 2007/0078416 | A1 | 4/2007 | Eliasen |
| 2007/0083156 | A1 | 4/2007 | Muto et al. |
| 2007/0161958 | A1 | 7/2007 | Glenn |
| 2007/0179456 | A1 | 8/2007 | Glenn |
| 2007/0208313 | A1 | 9/2007 | Conlon et al. |
| 2007/0219510 | A1 | 9/2007 | Zinn et al. |
| 2007/0232997 | A1 | 10/2007 | Glenn |
| 2007/0233017 | A1 | 10/2007 | Zinn et al. |
| 2007/0233018 | A1 | 10/2007 | Bizup et al. |
| 2007/0255234 | A1 | 11/2007 | Haase et al. |
| 2007/0270770 | A1 | 11/2007 | Bizup |
| 2007/0276344 | A1 | 11/2007 | Bizup et al. |
| 2007/0282308 | A1 | 12/2007 | Bell |
| 2008/0048855 | A1 | 2/2008 | Berger |
| 2008/0086075 | A1 | 4/2008 | Isik et al. |
| 2008/0108942 | A1 | 5/2008 | Brister et al. |

(56) References Cited

U.S. PATENT DOCUMENTS

| | | | |
|---|---|---|---|
| 2008/0114308 | A1 | 5/2008 | di Palma et al. |
| 2008/0132946 | A1 | 6/2008 | Mueller |
| 2008/0208236 | A1 | 8/2008 | Hobbs et al. |
| 2008/0249509 | A1 | 10/2008 | Glenn |
| 2008/0281279 | A1 | 11/2008 | Hoendervoogt et al. |
| 2008/0319399 | A1 | 12/2008 | Schweikert et al. |
| 2008/0319405 | A1 | 12/2008 | Bizup |
| 2009/0024024 | A1 | 1/2009 | Zinn |
| 2009/0024098 | A1 | 1/2009 | Bizup et al. |
| 2009/0076466 | A1 | 3/2009 | Quebbemann et al. |
| 2009/0099526 | A1 | 4/2009 | Powley et al. |
| 2009/0105688 | A1 | 4/2009 | McIntyre et al. |
| 2009/0118683 | A1 | 5/2009 | Hanson et al. |
| 2009/0156928 | A1 | 6/2009 | Evans et al. |
| 2009/0192467 | A1 | 7/2009 | Hansen et al. |
| 2009/0204074 | A1 | 8/2009 | Powers et al. |
| 2009/0221976 | A1 | 9/2009 | Linden |
| 2009/0259164 | A1 | 10/2009 | Pages et al. |
| 2010/0042073 | A1 | 2/2010 | Oster et al. |
| 2010/0121283 | A1 | 5/2010 | Hamatake et al. |
| 2010/0121313 | A1 | 5/2010 | Goode et al. |
| 2010/0298684 | A1 | 11/2010 | Leach et al. |
| 2011/0034886 | A1 | 2/2011 | Elbe et al. |
| 2011/0118677 | A1 | 5/2011 | Wiley et al. |
| 2011/0257577 | A1 | 10/2011 | Lane et al. |
| 2011/0264058 | A1 | 10/2011 | Linden et al. |
| 2011/0319728 | A1 | 12/2011 | Petisce et al. |
| 2012/0172711 | A1 | 7/2012 | Kerr et al. |
| 2012/0283518 | A1 | 11/2012 | Hart |
| 2013/0030348 | A1 | 1/2013 | Lauer |
| 2013/0046224 | A1 | 2/2013 | Ravenscroft et al. |
| 2013/0150767 | A1 | 6/2013 | Tsyrulnykov et al. |
| 2013/0150811 | A1 | 6/2013 | Horgan |
| 2014/0024998 | A1 | 1/2014 | Prosl et al. |
| 2014/0207086 | A1 | 7/2014 | Stats et al. |
| 2014/0243789 | A1 | 8/2014 | Mehta et al. |
| 2015/0190622 | A1 | 7/2015 | Saab |
| 2015/0196704 | A1 | 7/2015 | Adler |
| 2015/0231369 | A1 | 8/2015 | Gray et al. |
| 2015/0250933 | A1 | 9/2015 | Kerkhoffs et al. |
| 2015/0258322 | A1 | 9/2015 | Young et al. |
| 2015/0265280 | A1 | 9/2015 | Blatter et al. |
| 2015/0273201 | A1 | 10/2015 | Tallarida et al. |
| 2015/0290446 | A1 | 10/2015 | Wiley et al. |
| 2015/0306300 | A1 | 10/2015 | Phillips et al. |
| 2015/0327844 | A1 | 11/2015 | Hong et al. |
| 2016/0001055 | A1 | 1/2016 | Bourne et al. |
| 2016/0067470 | A1 | 3/2016 | Silva Pires e Albuquerque |
| 2017/0143890 | A1 | 5/2017 | Nardeo |
| 2018/0078751 | A1 | 3/2018 | Fedor et al. |
| 2019/0070399 | A1 | 3/2019 | Casiello et al. |
| 2019/0232035 | A1 | 8/2019 | Fedor et al. |
| 2020/0323557 | A1 | 10/2020 | Chavan et al. |
| 2022/0395678 | A1 | 12/2022 | Fedor et al. |
| 2022/0401703 | A1 | 12/2022 | Gooch et al. |
| 2023/0032423 | A1 | 2/2023 | Fedor et al. |
| 2024/0269448 | A1 | 8/2024 | Densley et al. |

FOREIGN PATENT DOCUMENTS

| | | | |
|---|---|---|---|
| CA | 2551680 | A1 | 7/2005 |
| CN | 102271737 | A | 12/2011 |
| EP | 0229729 | A2 | 7/1987 |
| EP | 0366814 | A1 | 5/1990 |
| EP | 0809523 | A1 | 12/1997 |
| EP | 1047473 | A1 | 11/2000 |
| EP | 1056506 | A1 | 12/2000 |
| EP | 810893 | B1 | 7/2002 |
| EP | 2179763 | A1 | 4/2010 |
| EP | 2948121 | B1 | 11/2017 |
| JP | H05506591 | A | 9/1993 |
| JP | H07148206 | A | 6/1995 |
| JP | H08501008 | A | 2/1996 |
| JP | 2008531226 | A | 8/2008 |
| WO | 1991012838 | A1 | 9/1991 |
| WO | 1993005730 | A1 | 4/1993 |
| WO | 1994005246 | A1 | 3/1994 |
| WO | 9625196 | A1 | 8/1996 |
| WO | 1996029112 | A1 | 9/1996 |
| WO | 1997001370 | A1 | 1/1997 |
| WO | 1997006845 | A1 | 2/1997 |
| WO | 1998017337 | A1 | 4/1998 |
| WO | 1999034859 | A1 | 7/1999 |
| WO | 9942166 | A1 | 8/1999 |
| WO | 2000033901 | A1 | 6/2000 |
| WO | 2000044424 | A1 | 8/2000 |
| WO | 2000053245 | A1 | 9/2000 |
| WO | 2001026713 | A1 | 4/2001 |
| WO | 0180926 | A2 | 11/2001 |
| WO | 2002038460 | A1 | 5/2002 |
| WO | 2002066595 | A1 | 8/2002 |
| WO | 2003066126 | A2 | 8/2003 |
| WO | 2004004800 | A2 | 1/2004 |
| WO | 2004071555 | A2 | 8/2004 |
| WO | 2004091434 | A2 | 10/2004 |
| WO | 2004093970 | A1 | 11/2004 |
| WO | 2005068009 | A1 | 7/2005 |
| WO | 2006064753 | A1 | 6/2006 |
| WO | 2006078915 | A2 | 7/2006 |
| WO | 2006096686 | A1 | 9/2006 |
| WO | 2006116438 | A2 | 11/2006 |
| WO | 2006130133 | A1 | 12/2006 |
| WO | 2006134100 | A1 | 12/2006 |
| WO | 2007079024 | A2 | 7/2007 |
| WO | 2007082003 | A2 | 7/2007 |
| WO | 2007087460 | A2 | 8/2007 |
| WO | 2007092210 | A1 | 8/2007 |
| WO | 2007094898 | A2 | 8/2007 |
| WO | 2007098771 | A2 | 9/2007 |
| WO | 2007109164 | A2 | 9/2007 |
| WO | 2007126645 | A2 | 11/2007 |
| WO | 2007136538 | A2 | 11/2007 |
| WO | 2008048361 | A1 | 4/2008 |
| WO | 2008063226 | A2 | 5/2008 |
| WO | 2008140901 | A1 | 11/2008 |
| WO | 2008157763 | A1 | 12/2008 |
| WO | 2009002839 | A1 | 12/2008 |
| WO | 2009012385 | A1 | 1/2009 |
| WO | 2009035582 | A1 | 3/2009 |
| WO | 2009046439 | A2 | 4/2009 |
| WO | 2009108669 | A1 | 9/2009 |
| WO | 2012064881 | A2 | 5/2012 |
| WO | 2014017986 | A1 | 1/2014 |
| WO | 2014116810 | A1 | 7/2014 |
| WO | 2015179862 | A1 | 11/2015 |
| WO | 2019200304 | A1 | 10/2019 |
| WO | 2021061095 | A1 | 4/2021 |
| WO | 2021078488 | A1 | 4/2021 |
| WO | 2022235276 | A1 | 11/2022 |
| WO | 2023077276 | A1 | 5/2023 |

OTHER PUBLICATIONS

U.S. Appl. No. 17/763,154 filed Mar. 23, 2022 Final Office Action dated Jul. 25, 2025.

U.S. Appl. No. 17/890,184, filed Aug. 17, 2022 Non-Final Office Action dated Sep. 5, 2025.

U.S. Appl. No. 17/890,184, filed Aug. 17, 2022 Restriction Requirement dated Jun. 9, 2025.

U.S. Appl. No. 17/963,813, filed Oct. 11, 2022 Non-Final Office Action dated Oct. 21, 2025.

U.S. Appl. No. 17/963,813, filed Oct. 11, 2022 Restriction Requirement dated Jul. 23, 2025.

"Merge". Merriam-Webster Dictionary. https://www.merriam-webster.com/dictionary/merge. Access May 13, 2021. (Year: 2021).

Canaud, B. et al. "Dialock: a new vascular access device for extracorporeal renal replacement therapy. Preliminary clinical results"—Mar. 1999.

CN 201480005902.2 filed Jul. 23, 2015 Office Action dated Jan. 20, 2016.

CN 201480005902.2 filed Jul. 23, 2015 Office Action dated Jul. 19, 2016.

(56) References Cited

OTHER PUBLICATIONS

CN 201480005902.2 filed Jul. 23, 2015 Office Action dated May 12, 2017.
EP 14743846.9 filed Aug. 12, 2015 Extended European Search Report dated Oct. 10, 2016.
EP 14743846.9 filed Aug. 12, 2015 Intent to Grant dated Jun. 26, 2017.
EP 17870333.6 filed Jun. 7, 2019 Supplemental European Search Report dated May 26, 2020.
Goldstein, D. J. et al. "Implantable Left Ventricular Assist Devices" (Nov. 19, 1998).
JP 2015-555266 filed Jul. 22, 2015 Office Action dated May 2, 2018.
JP 2015-555266 filed Jul. 22, 2015 Office Action dated Oct. 12, 2017.
Moran, J. E. "Subcutaneous Vascular Access Devices" (Nov. 1, 2001).
PCT/CN2021/128248 filed Nov. 2, 2021 International Search Report and Written Opinion dated Apr. 25, 2022.
PCT/US2014/012721 filed Jan. 23, 2014 International Search Report and Written Opinion dated Apr. 14, 2014.
PCT/US2017/061179 filed Nov. 10, 2017 International Search Report and Written Opinion dated Jan. 22, 2018.
PCT/US2019/027301 filed Nov. 12, 2020 Extended European Search Report dated Oct. 11, 2021.
PCT/US2021/031407 filed May 7, 2021 International Search Report and Written Opinion dated Feb. 4, 2022.
PCTUS2019052477 filed Sep. 23, 2019 International Search Report and Written Opinion dated Mar. 11, 2020.
Rosenblatt, M. et al. "Efficacy and Safety Results with the LifeSite Hemodialysis Access System versus the Tesio-Cath Hemodialysis Catheter at 12 Months"—Mar. 2006.
Sandhu, J. Dialysis Ports: A New Totally Implantable Option for Hemodialysis Access—Jun. 2002.
U.S. Appl. No. 14/162,113, filed Jan. 23, 2014 Final Office Action dated Jul. 2, 2018.
U.S. Appl. No. 14/162,113, filed Jan. 23, 2014 Final Office Action dated May 25, 2017.
U.S. Appl. No. 14/162,113, filed Jan. 23, 2014 Non-Final Office Action dated Dec. 11, 2017.
U.S. Appl. No. 14/162,113, filed Jan. 23, 2014 Non-Final Office Action dated May 4, 2016.
U.S. Appl. No. 14/162,113, filed Jan. 23, 2014 Non-Final Office Action dated Nov. 22, 2016.
U.S. Appl. No. 14/162,113, filed Jan. 23, 2014 Notice of Allowance dated Aug. 14, 2019.
U.S. Appl. No. 15/809,879, filed Nov. 10, 2017 Final Office Action dated May 18, 2021.
U.S. Appl. No. 15/809,879, filed Nov. 10, 2017 Final Office Action dated Nov. 5, 2020.
U.S. Appl. No. 15/809,879, filed Nov. 10, 2017 Final Office Action dated Oct. 4, 2021.
U.S. Appl. No. 15/809,879, filed Nov. 10, 2017 Non-Final Office Action dated Jun. 10, 2020.
U.S. Appl. No. 15/809,879, filed Nov. 10, 2017 Notice of Allowance dated May 4, 2022.
U.S. Appl. No. 29/616,511, filed Sep. 6, 2017 Notice of Allowance dated Aug. 8, 2019.
U.S. Appl. No. 29/716,554, filed Dec. 10, 2019 Notice of Allowance dated Feb. 6, 2020.
U.S. Appl. No. 17/763,154, filed Mar. 23, 2022 Non-Final Office Action dated Feb. 11, 2025.

* cited by examiner

UPPER ARM PORT

PRIORITY

This application is a U.S. national stage application of International Application No. PCT/CN2021/128248, filed Nov. 2, 2021, which is incorporated by reference in its entirety into this application.

SUMMARY

Briefly summarized, embodiments disclosed herein are directed to a vascular access system configured to place a port and catheter assembly subcutaneously, for example in in a limb or an upper arm area, and associated methods thereof. Placing a catheter and port assembly often requires multiple steps including coupling the catheter to the port and forming multiple incisions sites. This can be particularly challenging to the clinician operating in the confined wetted environment of a subcutaneous tissue pocket, as well as causing discomfort to the patient. Miniaturization of the port and catheter assembly can improve patient comfort and facilitate accessing smaller vessels, for example those disposed in the patient's limbs such as the basilic vein in the upper arm area. However, these smaller systems can render certain steps of the placement, such as coupling the catheter to the port, unfeasible.

Disclosed herein is a vascular access system including, a catheter extending longitudinally and defining a catheter lumen, a port coupled to a proximal end of the catheter, the port defining a reservoir in fluid communication with the catheter lumen, an expansion kit including a sheath defining a sheath lumen configured to receive one or both of the catheter and the port therein, and a splitter disposed on the port configured to separate the sheath along a longitudinal axis as the sheath is urged proximally thereover.

In some embodiments, the sheath includes a tab extending from a proximal edge of the sheath, perpendicular to a longitudinal axis, and configured to facilitate grasping the sheath. In some embodiments, the sheath includes a tear line extending longitudinally from a proximal edge to a distal end of the sheath and configured to facilitate separation of the sheath therealong. In some embodiments, the port further includes a strain relief, and wherein the splitter is disposed on an outer surface of the strain relief. In some embodiments, the splitter includes a guide extending longitudinally from a surface of the port, and a blade disposed between an inner surface of the guide and an opposite outer surface of the port.

In some embodiments, the sheath includes an aperture extending through a wall thereof and communicating with the sheath lumen, the aperture configured to receive a portion of the guide therethrough to direct a portion of the sheath onto the blade. In some embodiments, the aperture has a rhomboid shape. In some embodiments, the port placement system further includes a second aperture disposed on the sheath opposite the first aperture, and a second splitter disposed opposite the first splitter across a central longitudinal axis, and configured to engage the second aperture. In some embodiments, the expansion kit further includes a dilator configured to fit within a sheath lumen, the dilator including a sharpened tip.

In some embodiments, the dilator is formed of a rigid or resilient material and includes a guidewire lumen extending longitudinally therethrough. In some embodiments, the dilator includes an elongate body extending longitudinally and a wedge disposed at a proximal end thereof, the wedge having an outer profile matching an outer profile of the port. In some embodiments, the port defines a top surface, bottom surface, proximal end surface and a distal end surface, the catheter extending from the distal end surface, and the proximal end surface including a first needle penetrable septum configured to provide access to the reservoir.

In some embodiments, the port body further includes a second needle penetrable septum disposed on the top surface and configured to provide access to the reservoir. In some embodiments, the port placement system further includes a guidewire configured to extend through the first needle penetrable septum, through the reservoir, and into the catheter lumen.

Also disclosed is a method of placing a port assembly having a port and a catheter including accessing a vasculature of a patient, advancing a guidewire into the vasculature of the patient, advancing an expansion kit subcutaneously over the guidewire, the expansion kit including a sheath disposed on a dilator, forming a subcutaneous tissue pocket with the expansion kit, removing the dilator proximally, placing the port assembly within a lumen of the sheath, splitting the sheath along a longitudinal axis with a splitter disposed on the port, and withdrawing the sheath proximally.

In some embodiments, the step of placing the port assembly further includes placing a portion of the catheter within a shaft of the sheath, and placing a port within a funnel of the sheath. In some embodiments, the dilator includes an elongate body extending longitudinally and a wedge disposed at a proximal end thereof. In some embodiments, the elongate body defines a diameter equal to an outer diameter of the catheter. In some embodiments, the wedge defines an outer profile equal to an outer profile of the port.

In some embodiments, the step of advancing an expansion kit subcutaneously further includes passing a guidewire through a guidewire lumen defined by the dilator and extending longitudinally between a proximal end and a distal end of the dilator. In some embodiments, the step of splitting the sheath includes separating the sheath along a tear line extending longitudinally. In some embodiments, the step of splitting the sheath includes engaging a splitter with an aperture of the sheath to guide the sheath onto a blade.

Also disclosed is a method of placing a port assembly subcutaneously including urging an expansion kit subcutaneously, placing the port assembly within a lumen of a sheath of the expansion kit, urging the sheath proximally over a port of the port assembly, engaging a portion of the sheath with a splitter disposed on the port, and splitting the sheath along a longitudinal axis.

In some embodiments, the step of engaging a portion of the sheath with a splitter further includes extending a guide portion of the splitter through an aperture and directing the portion of the sheath on to a blade. In some embodiments, the aperture is rhomboid shaped. In some embodiments, urging an expansion kit subcutaneously includes urging a distal tip into a vasculature of a patient. In some embodiments, urging an expansion kit subcutaneously includes urging a wedge disposed at a proximal end of a dilator of the expansion kit subcutaneously to form a tissue pocket configured to receive the port of the port assembly. In some embodiments, the splitter is disposed on a strain relief of the port assembly.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DESCRIPTION

Figure 1:
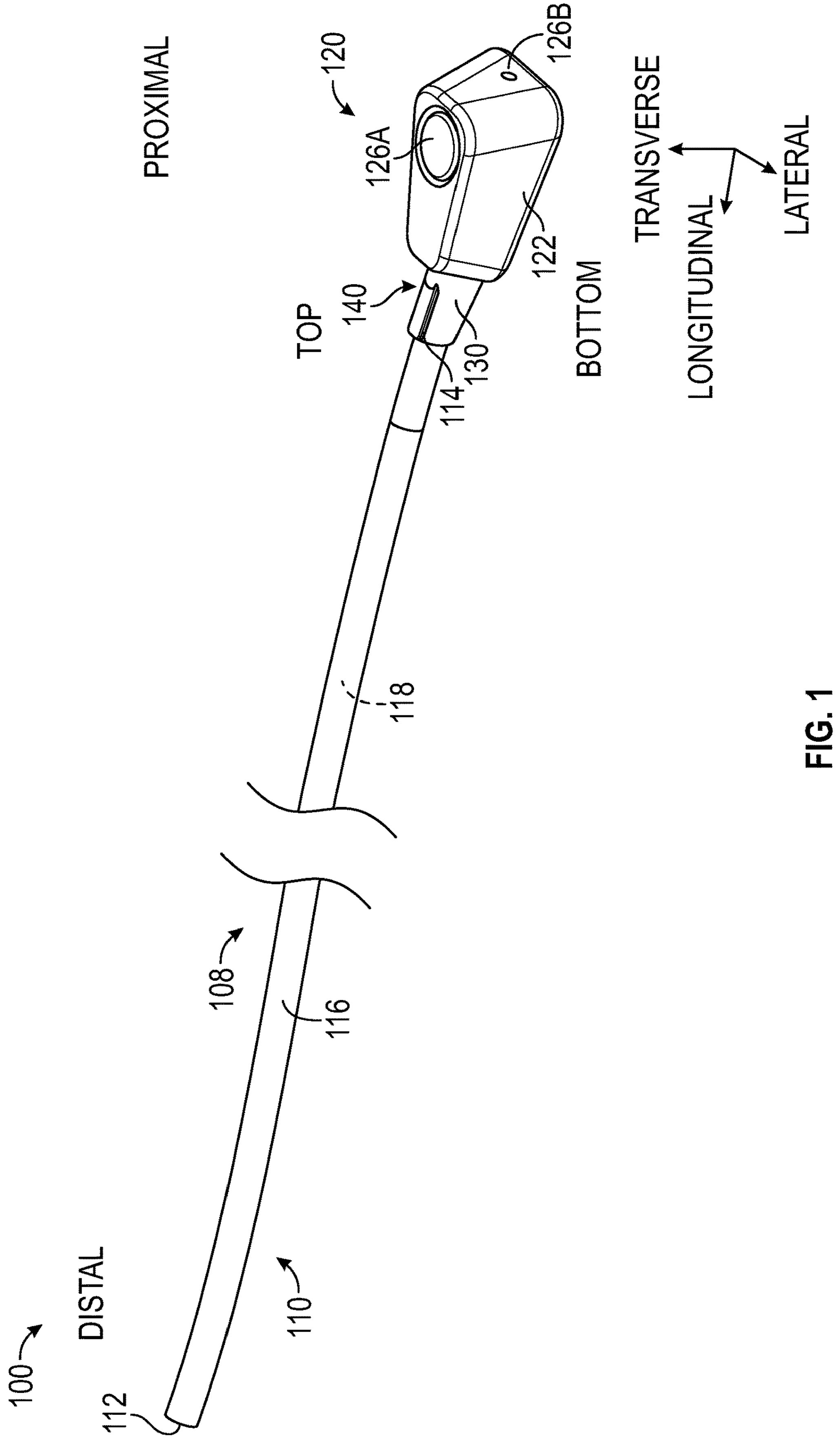
FIG. 1 shows a perspective view of a port and catheter assembly of a vascular access system, in accordance with embodiments disclosed herein.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, “first,” “second,” and “third” features or steps need not necessarily appear in that order, and the particular embodiments including such features or steps need not necessarily be limited to the three features or steps. Labels such as “left,” “right,” “top,” “bottom,” “front,” “back,” and the like are used for convenience and are not intended to imply, for example, any particular fixed location, orientation, or direction. Instead, such labels are used to reflect, for example, relative location, orientation, or directions. Singular forms of “a,” “an,” and “the” include plural references unless the context clearly dictates otherwise.

With respect to “proximal,” a “proximal portion” or a “proximal end portion” of, for example, a catheter disclosed herein includes a portion of the catheter intended to be near a clinician when the catheter is used on a patient. Likewise, a “proximal length” of, for example, the catheter includes a length of the catheter intended to be near the clinician when the catheter is used on the patient. A “proximal end” of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to “distal,” a “distal portion” or a “distal end portion” of, for example, a catheter disclosed herein includes a portion of the catheter intended to be near or in a patient when the catheter is used on the patient. Likewise, a “distal length” of, for example, the catheter includes a length of the catheter intended to be near or in the patient when the catheter is used on the patient. A “distal end” of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

To assist in the description of embodiments described herein, as shown in FIG. 1, a longitudinal axis extends substantially parallel to an axial length of the catheter. A lateral axis extends normal to the longitudinal axis, and a transverse axis extends normal to both the longitudinal and lateral axes. As used herein, a horizontal plane extends along the lateral and longitudinal axes. A vertical plane extends normal to the horizontal plane.

Unless defined otherwise, all technical and scientific terms used herein have the same meaning as commonly understood by those of ordinary skill in the art.

Embodiments described herein are directed to a vascular access system (“system”) 100 configured to provide access to a vasculature of a patient. In an embodiment, the system 100 can provide vascular access in a limb such as an arm or leg area. More specifically, the vascular access system can be configured to access a basilic vein of an upper arm area. However, it will be appreciated that the system 100 can provide vascular access to other areas of a patient’s body, without limitation. As shown in FIGS. 1-6, the system 100 can generally include a port and catheter assembly (“port assembly”) 108 comprising a catheter 110 coupled to a port 120, or similar subcutaneous access device (FIG. 1), and an expansion kit 158 comprising a sheath 160 and a dilator 180 (FIG. 5A).

The catheter 110 of the port assembly 108 can include a catheter body 116 defining a catheter lumen 118 and extending between a distal tip 112 and a proximal end 114. In an embodiment, the proximal end 114 of the catheter 110 can be formed integrally with the port 120. In an embodiment, the port assembly 108 can further include a strain relief 130 disposed over the connection between the catheter 110 and the port 120, or can be disposed between the catheter 110 and the port 120 and formed integrally therewith. In an embodiment, the proximal end 114 of the catheter 110 can be selectively coupled with the port 120. Optionally, a cathlock or similar device can further secure the catheter 110 to the port 120. Optionally, the proximal end 114 of the catheter 110 may be trimmable prior to coupling the catheter 110 with the port 120. In an embodiment, the catheter 110 can be formed of a flexible material configured to negotiate tortuous vascular pathways. In an embodiment, the catheter 110 can be formed of a plastic, polymer, elastomer, rubber, silicone rubber, or the like.

In an embodiment, the port 120 can generally include a body 122 defining a reservoir 124 that is in fluid communication with the lumen 118 of the catheter 110. The port 120 can further include one or more needle penetrable septa 126 configured to provide access to one or both of the reservoir 124 and the catheter lumen 118. In an embodiment, an access needle can extend percutaneously, through the needle-penetrable septum 126 and into the reservoir 124 to provide fluid communication therewith. In an embodiment, the port body 122 can be 20 mm long along the longitudinal axis, 10 mm high along the transverse axis, and 10 mm wide along the lateral axis. However, it will be appreciated that these measurements are exemplary and not intended to be limiting, and greater or lesser dimensions of the port body 122 are also contemplated to fall within the scope of the present invention.

In an embodiment, the port assembly 108 can further include a splitter device ("splitter") 140 disposed on the strain relief 130. It will be appreciated, however, that the splitter 140 can be disposed on other portions of the port assembly 108, for example the port body 122 or a portion of the catheter 110, or the like. The splitter 140 can be configured to facilitate separation of the sheath 160 of the expansion kit 158, as described in more detail herein.

Figure 2:
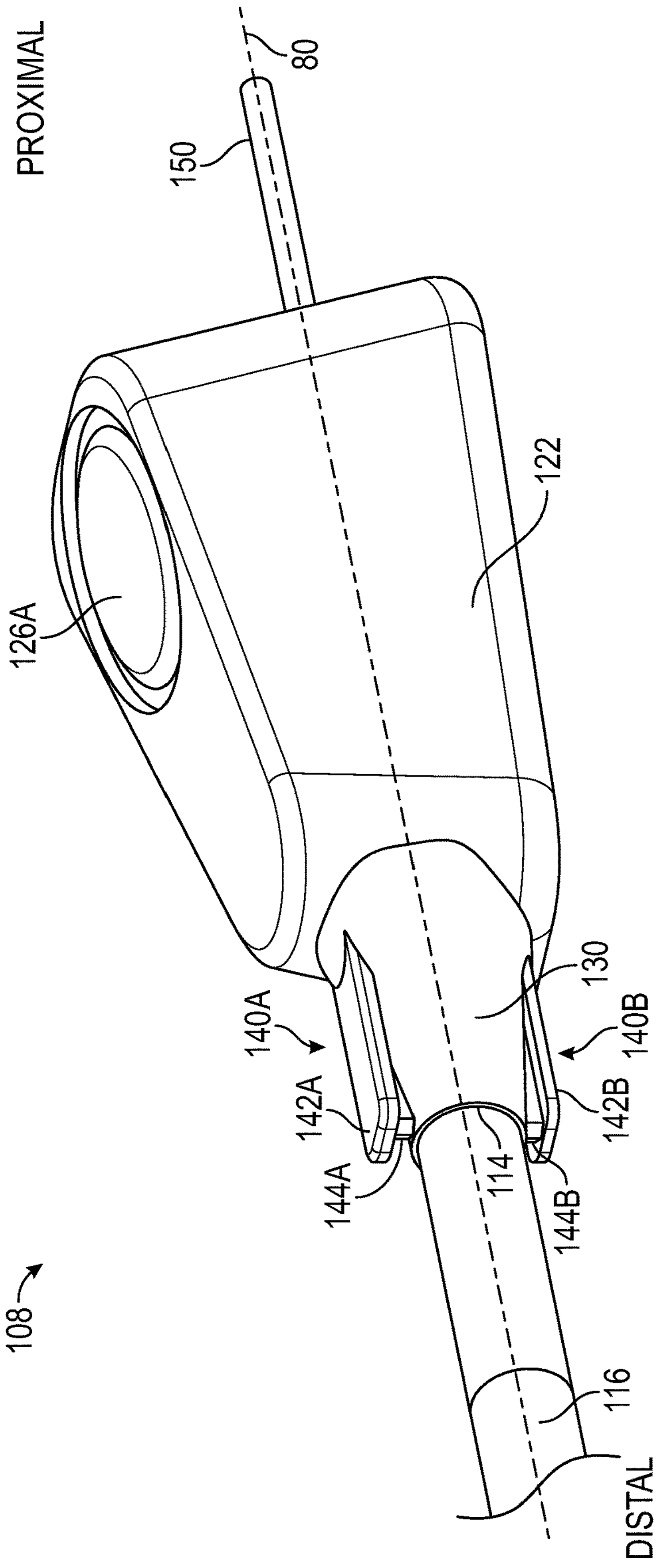
FIG. 2 shows a perspective view of the port of FIG. 1, in accordance with embodiments disclosed herein.
Figure 3:
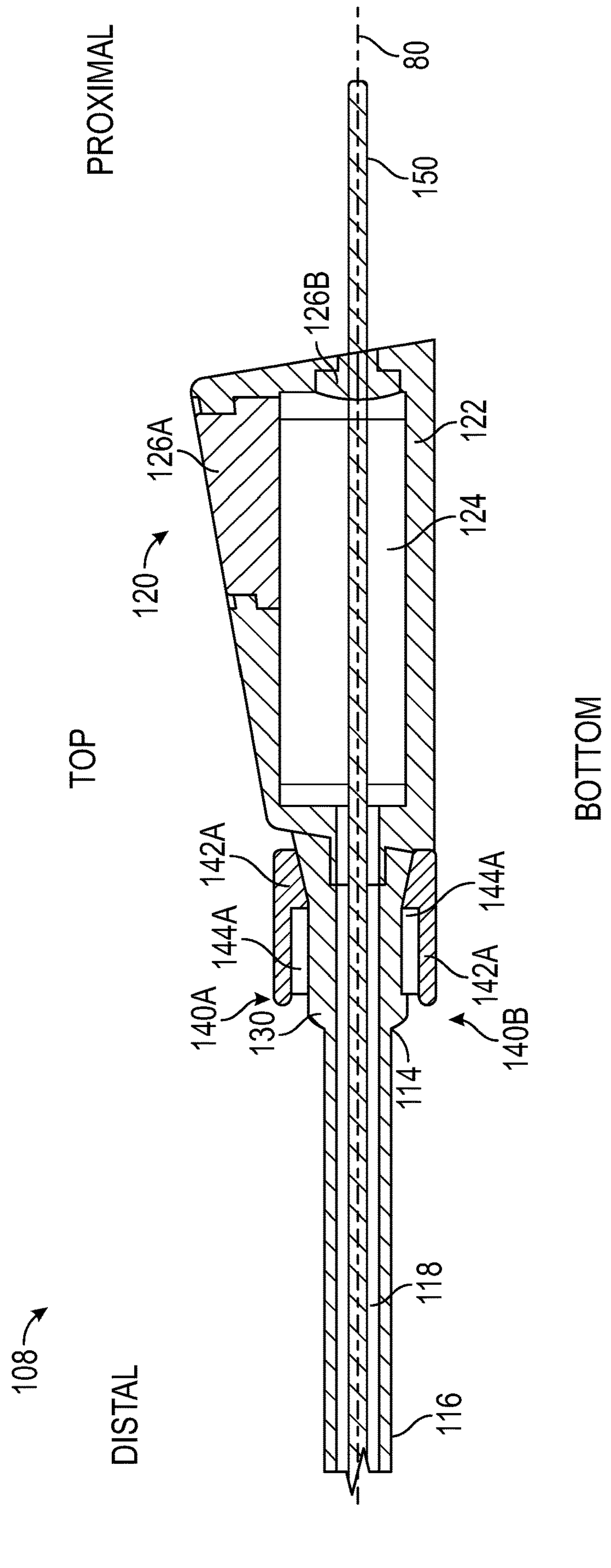
FIG. 3 shows a cross-section view of a port of a vascular access system, in accordance with embodiments disclosed herein.

In an embodiment, as shown in FIGS. 2-3, the splitter 140 can include a guide 142 and a blade 144. The guide 142 can extend from an outer surface of the strain relief 130 substantially parallel to a longitudinal axis, and can include a chamfered or beveled distal end. In an embodiment, the guide 142 can be formed of the same material as one of the catheter 110, port 120, or the strain relief 130. In an embodiment, the guide can be formed of a compliant or flexible material. In an embodiment, the guide 142 can be formed of a plastic, polymer, elastomer, rubber, silicone rubber, or the like.

In an embodiment, the blade 144 can extend radially from an outer surface of the strain relief 130 and can extend parallel to a longitudinal axis. A distal edge of the blade 144 can be sharpened to facilitate separating the sheath 160 as the sheath 160 is urged thereover, as described in more detail herein. In an embodiment, the blade 144 can be disposed between the outer surface of the strain relief 130 and an inner surface of the guide 142. The guide 142 can support the blade 144 positioned as such. In an embodiment, the blade 144 can be formed of a substantially rigid or resilient material, such as a plastic, polymer, metal, alloy, composite, or the like.

In an embodiment, the port assembly 108 can include one or more splitters 140. For example, as shown in FIGS. 2-3, the system 100 can include a first splitter 140A disposed on a top surface of the strain relief 130 and a second splitter 140B disposed on a bottom surface of the strain relief 130. It will be appreciated that other numbers or configurations of splitter 140 are also contemplated to fall within the scope of the present invention.

Figure 4:
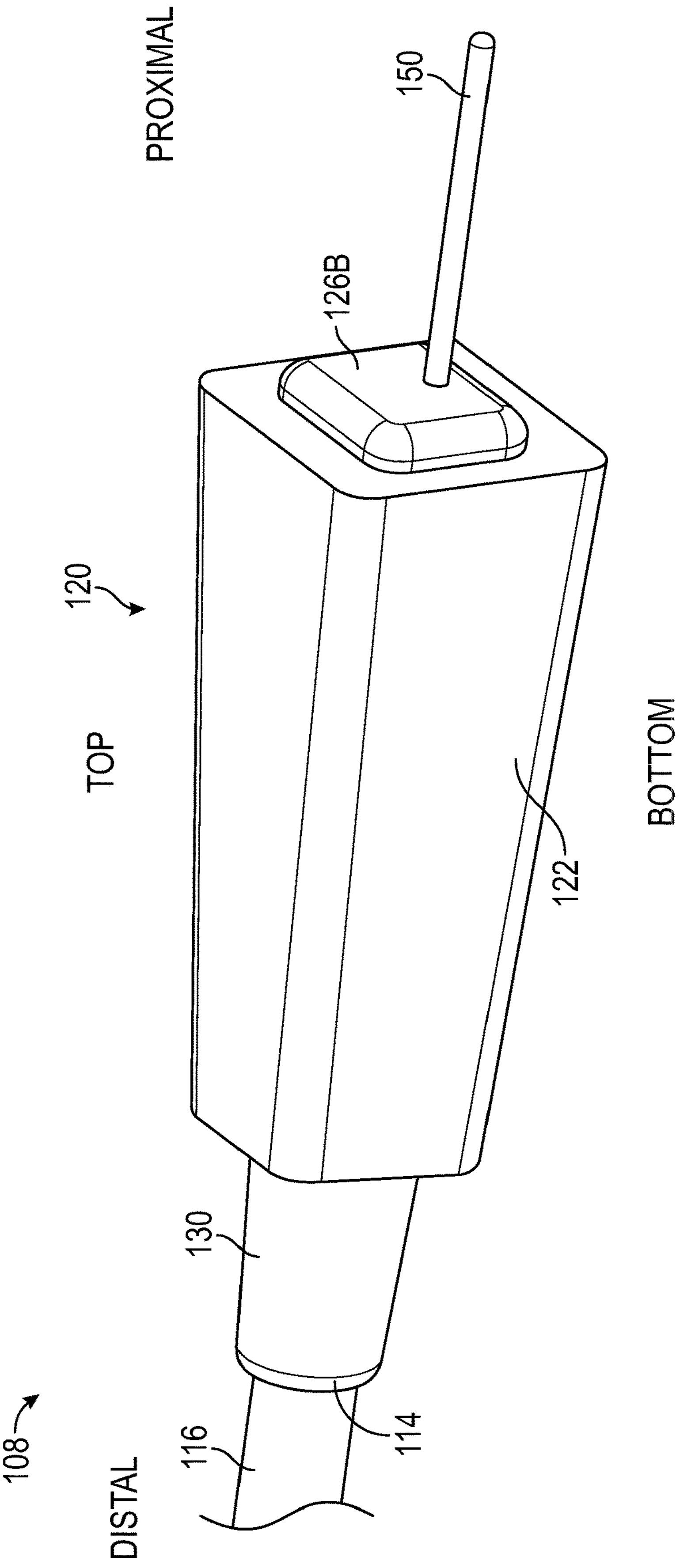
FIG. 4 shows a perspective view of a port of a vascular access system, in accordance with embodiments disclosed herein.
Figures 5A, 5B:
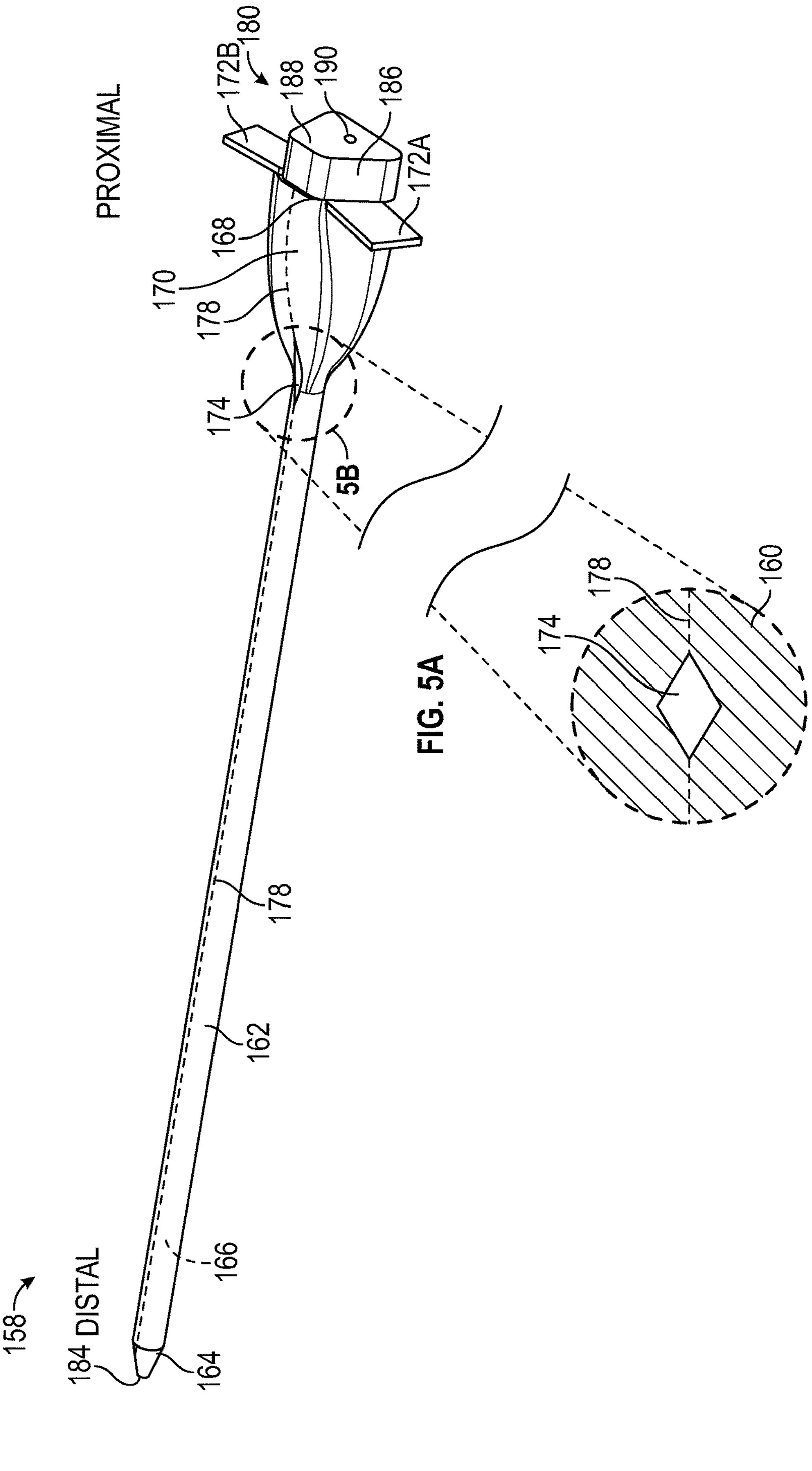
FIG. 5A shows a perspective view of an expansion kit of a vascular access system, in accordance with embodiments disclosed herein.
FIG. 5B shows close up detail of the expansion kit of FIG. 5A, in accordance with embodiments disclosed herein.

In an embodiment, as shown in FIGS. 2-4 the port 120 can include a septum 126 disposed on one or both of the top surface and a proximal surface of the port body 122 and configured to provide access to one or both the reservoir 124 and the catheter lumen 118. In an embodiment, the port 120 can include a first septum 126A disposed on a top surface of the port body 122 and a second septum 126B disposed on a proximal surface of the port body 122. As used herein, a "septum" can include a needle penetrable septum, valve, slit valve, or the like formed of a silicone rubber or similar material and configured to receive an elongate medical device, needle, guidewire, or similar device therethrough while also controlling a fluid flow therethrough.

As shown in FIGS. 3-4, in an embodiment, the second septum 126B disposed on the proximal surface, can align with a central longitudinal axis 80 of the catheter lumen 118. In an embodiment, the vascular access system 100 can further include a guidewire 150. The guidewire 150 can be configured to extend through the second septum 126B, through the reservoir 124 and into the catheter lumen 118, as described in more detail herein. In an embodiment, an access needle can be configured to extend through one of the first septum 126A or the second septum 126B to provide fluid communication with the reservoir 124.

Figure 6:
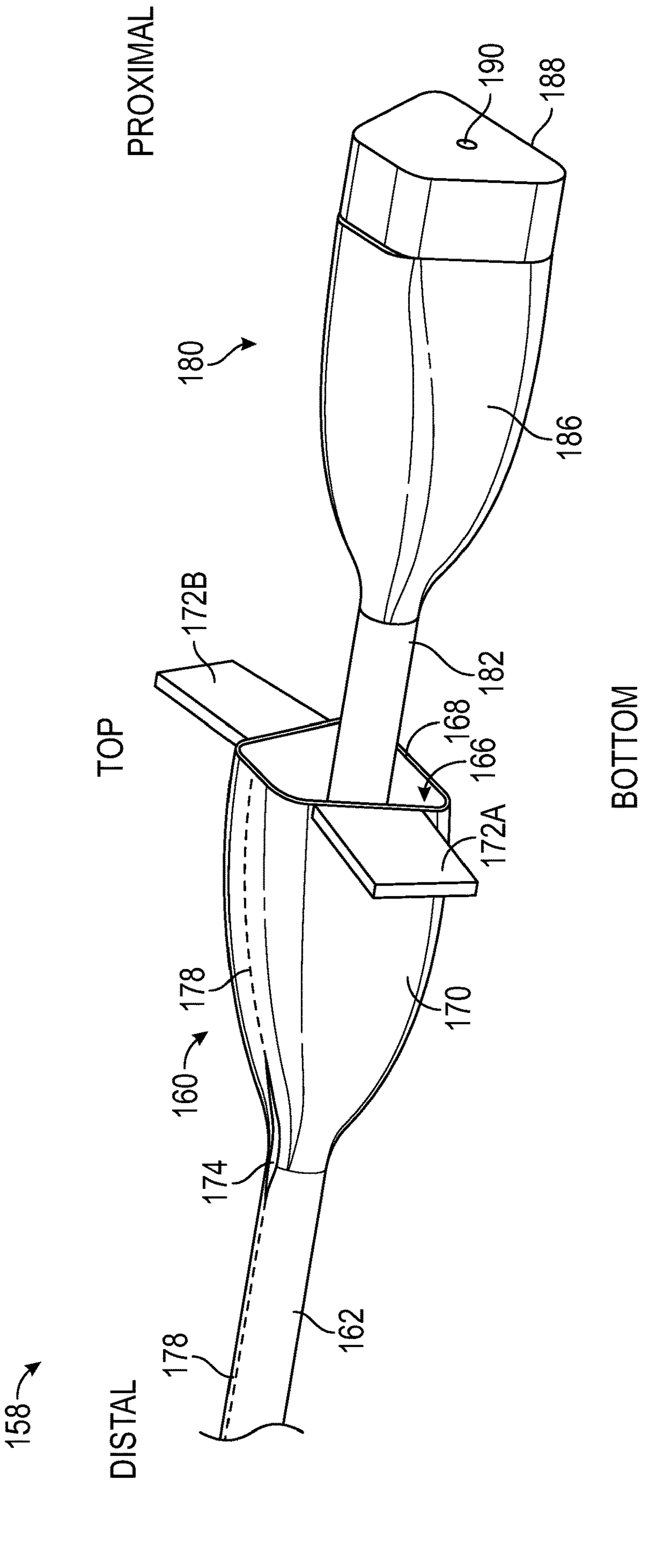
FIG. 6 shows an exploded view of an expansion kit of a vascular access system, in accordance with embodiments disclosed herein.

FIGS. 5A-6 show further details of the expansion kit 158 of the vascular access system 100. The expansion kit 158 can generally include a sheath 160 having a shaft 162 extending longitudinally, and a funnel 170 disposed at a proximal end thereof. The sheath 160 can be formed of a compliant or flexible material including a plastic, polymer, elastomer, rubber, silicone rubber, or the like. The sheath 160 can define a lumen 166 extending from a distal end 164 of the sheath 160 to a proximal end 168. The shaft 162 can define a substantially cylindrical shape and can be configured to receive a portion of one of the dilator 180 or the catheter 110 therein. In an embodiment, a distal end 164 of the sheath 160 can be open. As such a distal tip 112 of the catheter 110 or a distal tip 184 of the dilator 180 can extend distally of the distal end 164 of the sheath 160, as described in more detail herein. In an embodiment, a distal tip 164 of the sheath 160 can be closed.

In an embodiment, the sheath 160 include a funnel 170 coupled to a proximal end of the shaft 162. The funnel 170 can define a substantially tapered portion of the lumen 166 and can be configured to receive a portion of the port 120 therein. In an embodiment, an inner profile of the funnel 170 can match an outer profile of the port body 122. In an embodiment, the funnel 170 can be elastically or malleably deformable to match an outer profile of the port body 122. In an embodiment, the funnel 170 can be formed of the same material as the shaft 132. In an embodiment, the funnel 170 can be formed of a different material and can display different mechanical properties from that of the shaft 132.

In an embodiment, the sheath 160 can include a tear line 178 extending longitudinally along at least a portion thereof. In an embodiment, the tear line 178 can extend between a distal end 164 and a proximal end 168 of the sheath 160. In an embodiment, the tear line 178 can be a groove, score line, perforation, laser cut line, or similar line of weakness configured to facilitate separation of the sheath 160 therealong. In an embodiment, the sheath 160 can include a first tear line 178 extending along a top surface of the sheath 160 and a second tear line 178 extending along a bottom surface of the sheath 160. However, it will be appreciated that other numbers and configurations of tear line 178 are contemplated to fall within the scope of the present invention.

In an embodiment, the sheath 160 can include one or more pull tabs 172, for example a first pull tab 172A and a second pull tab 172B. The one or more pull tabs 172 can be configured to facilitate grasping the sheath 160 and urging a first portion radially outward from a second portion and facilitate separating the sheath 160 along a longitudinal axis, e.g. along the tear line 178. In an embodiment, the first pull tab 172A and the second pull tab 172B can extend radially from sheath 160. In an embodiment, the first pull tab 172A and the second pull tab 172B can be disposed opposite each other across the central longitudinal axis 80. For example, the first pull tab 172A and the second pull tab 172B can extend laterally from a proximal portion, e.g. a proximal end 168, of the sheath 160.

In an embodiment, the sheath 160 can include an aperture 174, extending through a wall thereof and communicating with the sheath lumen 166. The aperture 174 can define a substantially rhomboid shape, however, it will be appreciated that other regular or irregular closed curve shapes are also contemplated. In an embodiment, as shown in FIG. 5B the aperture 174 can be aligned with a tear line 178. In an embodiment, one or more inflection points of the aperture 174 can align with the tear line 178.

Figure 7:
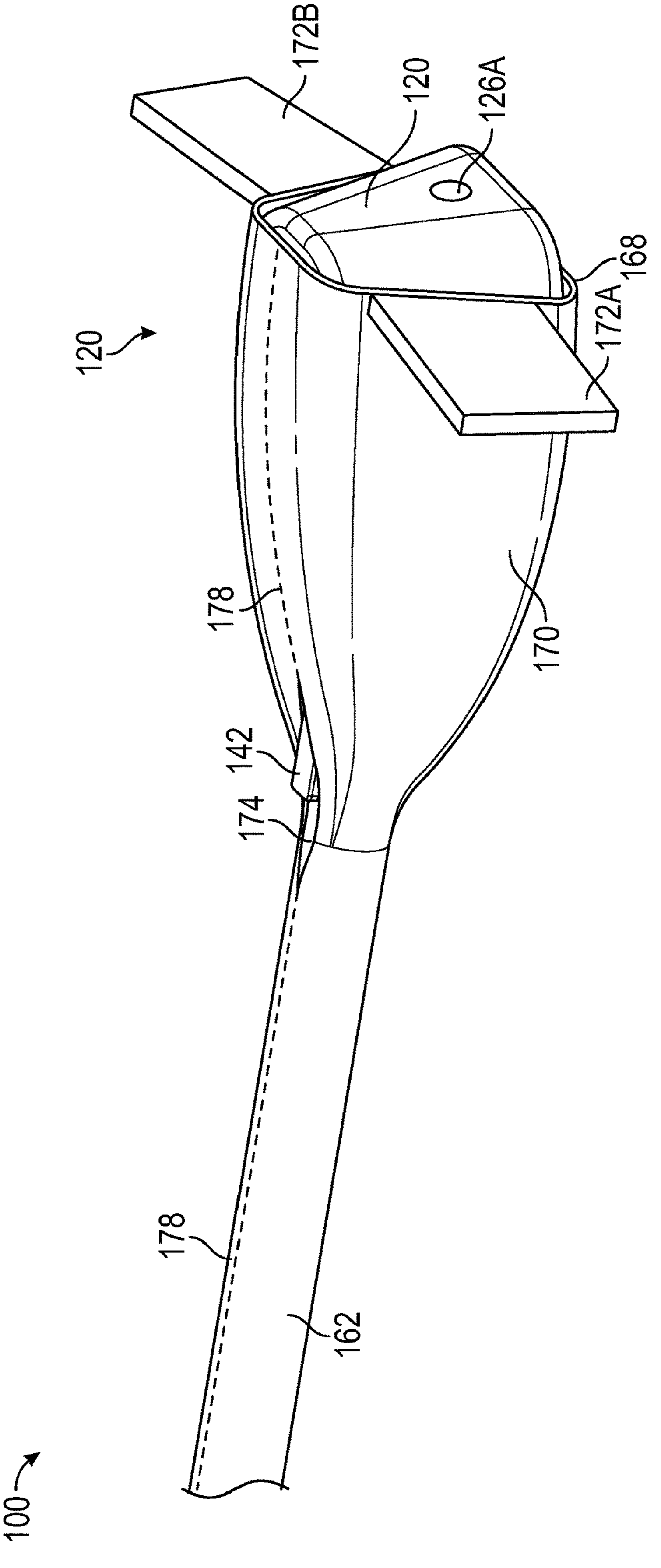
FIG. 7 shows close up detail of a port disposed within a sheath of the expansion kit, in accordance with embodiments disclosed herein.

In an embodiment, as shown in FIG. 7, a port assembly 108 can be advanced distally into the sheath lumen 166. The catheter 110 can extend through a portion of the lumen 166 defined by the shaft 162. Optionally a distal tip 112 thereof can extend distally of a distal end 164 of the sheath 166. As the port 120 is received within the funnel 170, the guide 142 of the splitter 140 can align with, and extend through, the aperture 174. In an embodiment, the sheath 160 can be urged proximally relative to the port assembly 108. As such, a distal end of the aperture 174 can be directed by the guide 142 onto the blade 144. As the shaft 162 is urged proximally over the splitter 140, the blade 144 can facilitate separation of the shaft 162 along a longitudinal axis and allow the separate portions of the shaft 162 to be urged proximally past the port 120.

As shown in FIGS. 5A-6, the expansion kit 158 can further include a dilator 180. The dilator 180 can be formed of a substantially rigid, or resilient, material including a plastic, polymer, metal, alloy, composite, combinations thereof, or the like. The dilator 180 can include an elongate body 182 configured to extend through the sheath lumen 166. In an embodiment, a distal tip 184 of the dilator 180 can extend distally of the distal end 164 of the sheath 160. In an embodiment, the distal tip 184 of the dilator 180 can define a tapered shape and/or a sharpened tip configured to facilitate separating tissues as the expansion kit 158 is urged subcutaneously.

In an embodiment, the dilator 180 can include a wedge 168 disposed at a proximal end thereof. The wedge 180 can define a substantially tapered shape. In an embodiment, the wedge 186 can define an outer profile that matches one or both of an outer profile of the port 120 and an inner profile of a portion of the lumen 166 defined by the funnel 170. As will be appreciated, the wedge 186 can define various regular or irregular three-dimensional shapes without departing from the spirit of the invention. In an embodiment, an outer profile of the dilator 180 can substantially match one or both of an inner profile of the sheath lumen 166 and an outer profile of the port assembly 108. As such, urging the expansion kit 158 subcutaneously can separate the tissues and define a tissue pocket configured to receive the port assembly 108 therein. In an embodiment, the dilator 180 can include a guidewire lumen 190 extending between a proximal end 188 of the dilator 180 and a distal tip 184 and configured to receive a guidewire 150 therethrough.

Figure 8A:
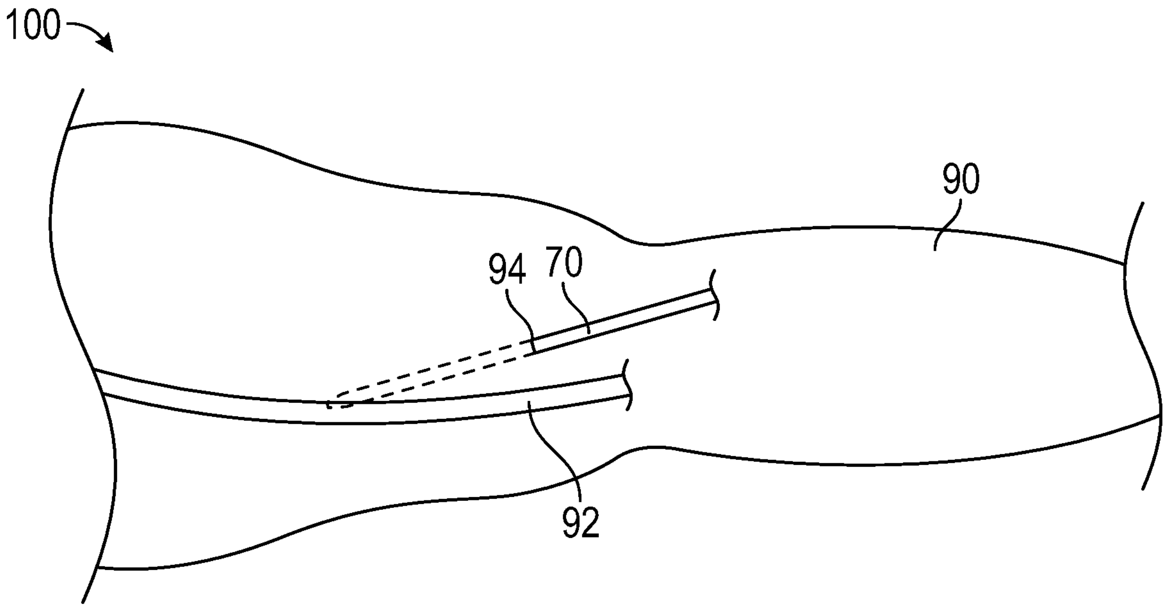
FIGS. 8A-8F shows an exemplary method of use for a vascular access system, in accordance with embodiments disclosed herein.
Figure 8B:
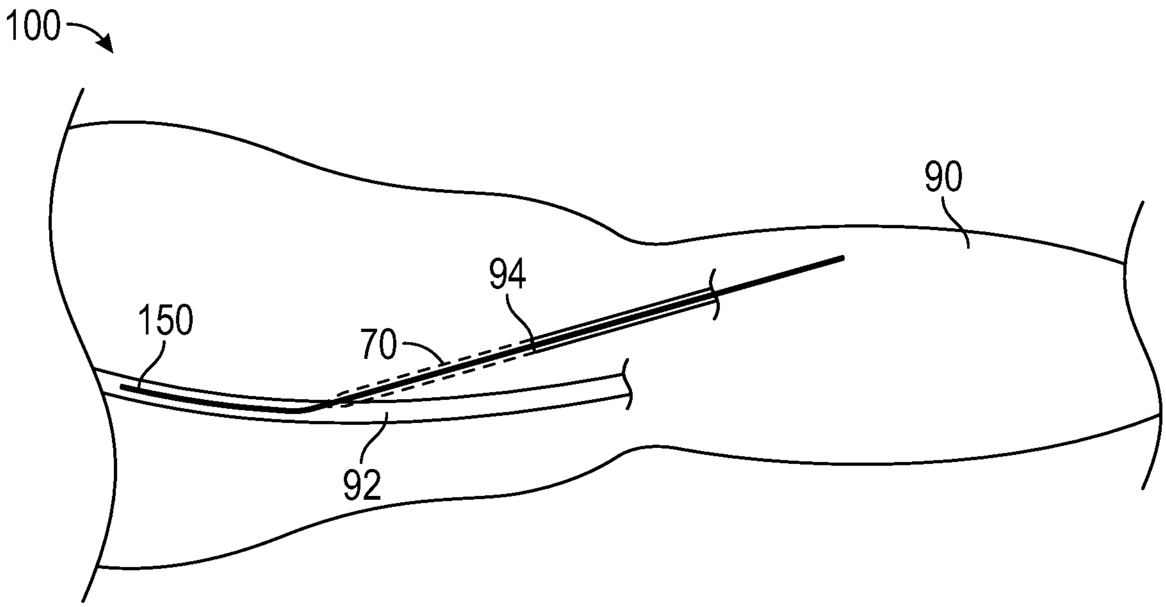

In an exemplary method of use, as shown in FIGS. 8A-8F, a vascular access system 100 is provided, as described herein. As shown in FIG. 8A, a user can form an insertion site 94 using a scalpel or by advancing a needle 70 distally to pierce a skin surface. In an embodiment, the user can advance the needle 70 to access the vasculature 92 of the patient, for example a basilic vein 92 of an upper arm 90. However, it will be appreciated that other areas of the body are contemplated. In an embodiment, the user can be guided under ultrasonic imaging, or similar medical imaging techniques to access the vasculature 92 with the needle 70. As shown in FIG. 8B, a user can then advance a guidewire 150 through the needle lumen and into the vasculature 92 to maintain patency of the access site. The needle 70 can then be withdrawn proximally over the guidewire 150.

Figure 8C:
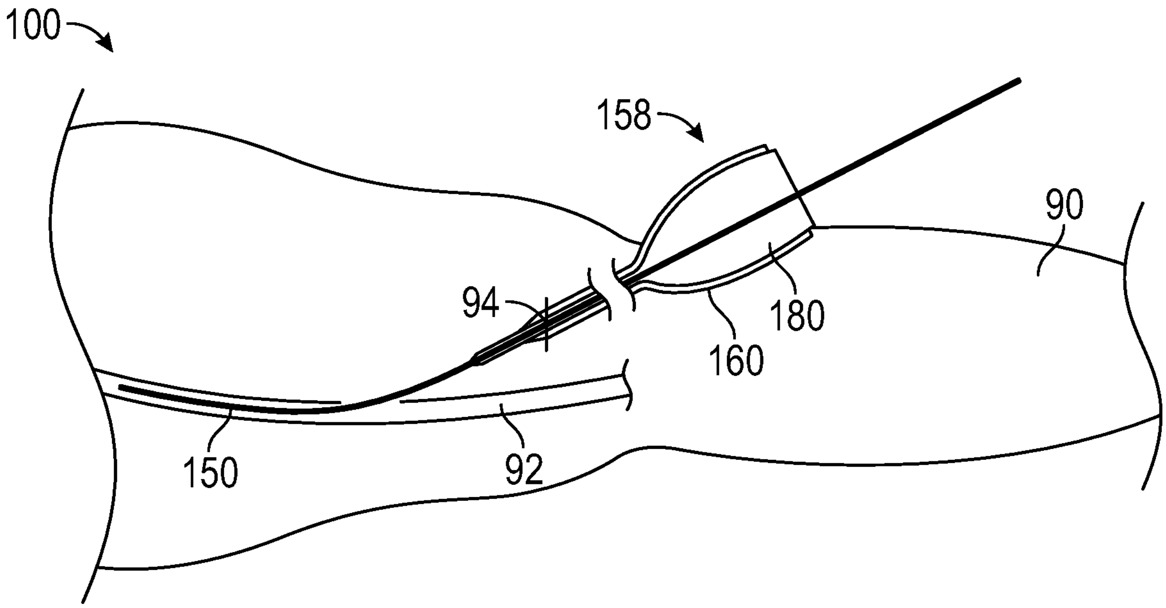

As shown in FIG. 8C, a user can then advance an expansion kit 158 over the guidewire 150, through the insertion site 94 and into the vasculature 92. Optionally, a user can widen the insertion site 94 at the skin surface using a scalpel or the like, prior to inserting the expansion kit 158. The distal tip 184 of the dilator can define a sharpened tip. Further, the shaft 162 can fit tightly about a portion of the dilator body 182. An outer diameter of the shaft 162 disposed on the dilator 180 can be larger than an outer diameter of one or both of the needle 70 and the catheter body 116. As such, the expansion kit 158 can widen one or more of the insertion site 94, the subcutaneous tissues surrounding the vessel 92, and an access site to the vessel 92 itself, sufficiently to receive the catheter 110, as described in more detail herein. In an embodiment, the dilator 180 can provide increased rigidity to facilitate urging the expansion kit 158 subcutaneously, and forming a pathway for the port assembly 108.

Figure 8D:
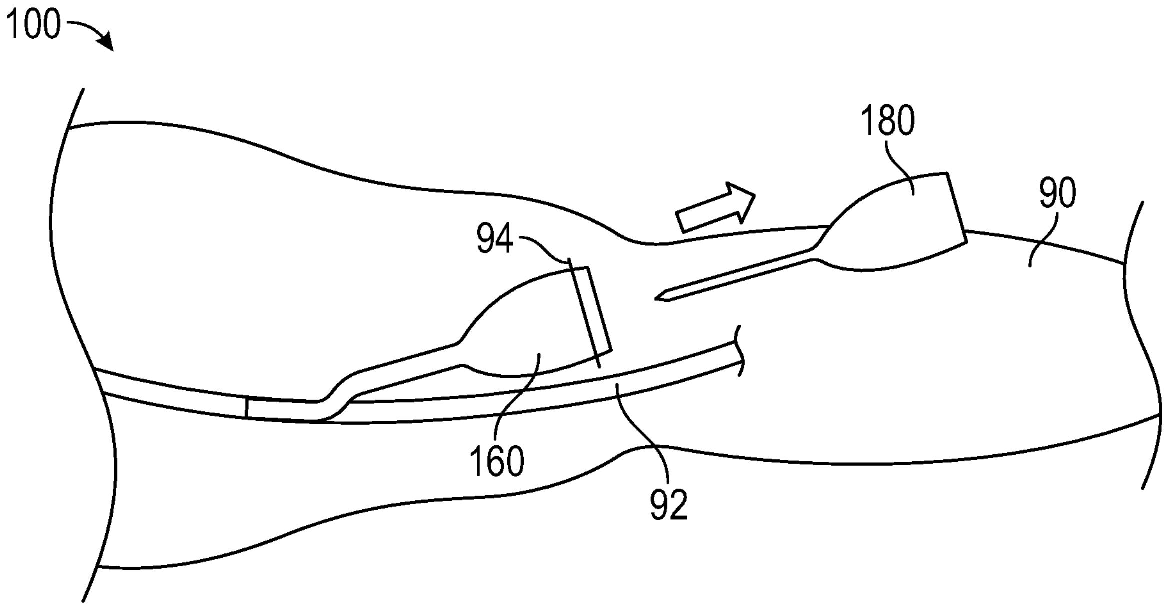

As shown in FIG. 8D, the expansion kit 158 can continue to be urged subcutaneously, until one or both of the funnel 170 and the wedge 186 portions of the expansion kit 158 are disposed subcutaneously. As will be appreciated, an outer diameter of the funnel 170 can be larger than an outer diameter of one or both of the port 120 and the shaft 162. As such, urging the funnel 170 subcutaneously can form a tissue pocket configured to receive the port 120 therein. With the sheath 160 placed subcutaneously, the dilator 180 and guidewire 150 can be withdrawn proximally from the sheath 160, either simultaneously or consecutively. The sheath 160 can be configured to maintain patency of the tissue pocket and the access site to the vasculature 92.

Figure 8E:
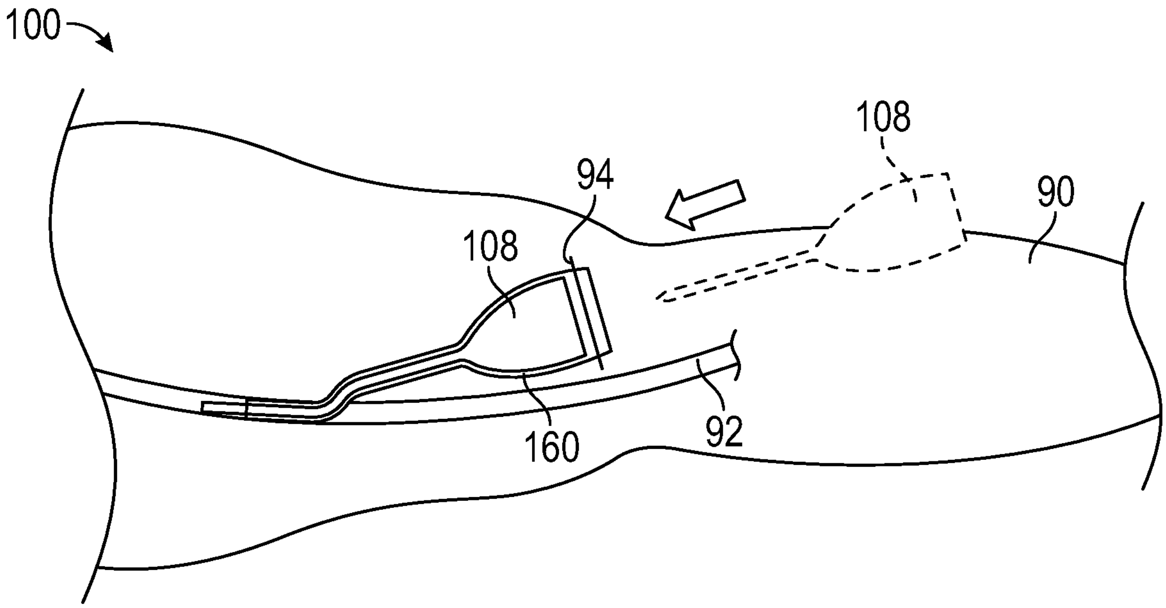

As shown in FIG. 8E, the port assembly 108 can then be advanced into the lumen 166 of the sheath 160. In an embodiment, the diameter of the sheath lumen 166 defined by the shaft 162 can be equal to or slightly larger than an outer diameter of the catheter 110. Similarly, the diameter of the sheath lumen 166 defined by the funnel 170 can be equal to or larger than the outer diameter of the port 120. As such the port assembly 108 can be received within the sheath lumen 166 with little or no resistance.

With the port assembly 108 placed subcutaneously, a user can grasp the sheath 160 using one or more tabs 172 and can urge the sheath 160 proximally over the port assembly 108. In an embodiment, the user can urged the tabs 172 radially outward relative to a central longitudinal axis 80, and separate the funnel 170 along a longitudinal axis. In an embodiment, the tear line 178 can facilitate separation of the funnel 170 along a longitudinal axis into a first portion and a second portion which can then be urged proximally either side of the port 120.

Figure 8F:
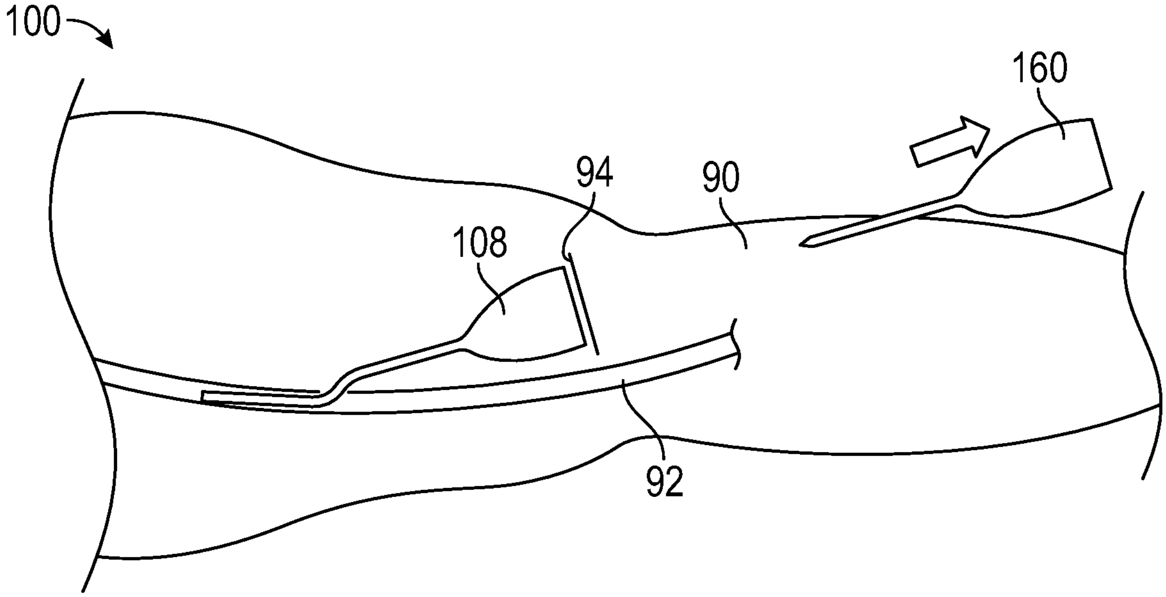

In an embodiment, the guide 142 can engage the aperture 174 and can direct a portion of the dilator shaft 162 on to the blade 144 to facilitate separating the shaft along a longitudinal axis. In an embodiment, the tear line 178 can align with the blade 144 and facilitate separation of the shaft 162 into a first portion and a second portion which can then be urged proximally either side of the port 120. The sheath 160 can then pass proximally past the port 120 and removed. As shown in FIG. 8F, with the port assembly placed subcutaneously and with a distal tip 112 of the catheter disposed within the vasculature 92 the insertion site 94 can be closed and the port 120 can be accessed percutaneously by an access needle.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A vascular access system, comprising:

a catheter extending longitudinally and defining a catheter lumen;

a port coupled to a proximal end of the catheter, the port defining a reservoir in fluid communication with the catheter lumen;

an expansion kit including a sheath defining a sheath lumen configured to receive one or both of the catheter and the port therein; and a first splitter disposed on the port configured to separate the sheath along a longitudinal axis as the sheath is urged proximally thereover;

wherein the splitter includes a guide extending longitudinally from a surface of the port, and a blade disposed between an inner surface of the guide and an opposite outer surface of the port; and wherein the sheath includes a first aperture extending through a wall thereof and communicating with the sheath lumen, the first aperture configured to receive a portion of the guide therethrough to direct a portion of the sheath onto the blade.

2. The vascular access system according to claim 1, wherein the sheath includes a tab extending from a proximal edge of the sheath, perpendicular to the longitudinal axis, and configured to facilitate grasping the sheath.

3. The vascular access system according to claim 1, wherein the sheath includes a tear line extending longitudinally from a proximal edge to a distal end of the sheath and configured to facilitate separation of the sheath therealong.

4. The vascular access system according to claim 1, wherein the port further includes a strain relief, and wherein the splitter is disposed on an outer surface of the strain relief.

5. The vascular access system according to claim 1, wherein the first aperture has a rhomboid shape.

6. The vascular access system according to claim 1, further including a second aperture disposed on the sheath opposite the first aperture, and a second splitter disposed opposite the first splitter across a central longitudinal axis, and configured to engage the second aperture.

7. The vascular access system according to claim 1, wherein the expansion kit further includes a dilator configured to fit within the sheath lumen, the dilator including a sharpened tip.

8. The vascular access system according to claim 7, wherein the dilator is formed of a rigid or resilient material and includes a guidewire lumen extending longitudinally therethrough.

9. The vascular access system according to claim 7, wherein the dilator includes an elongate body extending longitudinally and a wedge disposed at a proximal end thereof, the wedge having an outer profile matching an outer profile of the port.

10. The port placement system according to claim 1, wherein the port defines a top surface, a bottom surface, a proximal end surface and a distal end surface, the catheter extending from the distal end surface, and the proximal end surface including a first needle penetrable septum configured to provide access to the reservoir.

11. The vascular access system according to claim 10, wherein the port further includes a second needle penetrable septum disposed on the top surface and configured to provide access to the reservoir.

12. The vascular access system according to claim 10, further including a guidewire configured to extend through the first needle penetrable septum, through the reservoir, and into the catheter lumen.

13. A method of placing a port assembly having a port and a catheter, comprising:

accessing a vasculature of a patient;

advancing a guidewire into the vasculature of the patient;

advancing an expansion kit subcutaneously over the guidewire, the expansion kit including a sheath disposed on a dilator;

forming a subcutaneous tissue pocket with the expansion kit;

removing the dilator proximally;

placing the port assembly within a lumen of the sheath;

splitting the sheath along a longitudinal axis with a splitter disposed on the port; and withdrawing the sheath proximally;

wherein splitting the sheath includes engaging the splitter with an aperture of the sheath to guide the sheath onto a blade.

14. The method according to claim 13, wherein placing the port assembly further includes placing a portion of the catheter within a shaft of the sheath, and placing the port within a funnel of the sheath.

15. The method according to claim 13, wherein the dilator includes an elongate body extending longitudinally and a wedge disposed at a proximal end thereof.

16. The method according to claim 15, wherein the elongate body defines a diameter equal to an outer diameter of the catheter.

17. The method according to claim 15, wherein the wedge defines an outer profile equal to an outer profile of the port.

18. The method according to claim 13, wherein advancing the expansion kit subcutaneously further includes passing the guidewire through a guidewire lumen defined by the dilator and extending longitudinally between a proximal end and a distal end of the dilator.

19. The method according to claim 13, wherein splitting the sheath includes separating the sheath along a tear line extending longitudinally.

* * * * *